United States Patent
Sabota et al.

(10) Patent No.: US 10,555,858 B2
(45) Date of Patent: Feb. 11, 2020

(54) INFANT CARE TRANSPORT DEVICE WITH SHOCK AND VIBRATION SYSTEM

(71) Applicant: Segars California Partners, LP, Austin, TX (US)

(72) Inventors: Peter D. Sabota, Austin, TX (US); Reza Aghili, Cedar Park, TX (US)

(*) Notice: Subject to any disclaimer, the term of this patent is extended or adjusted under 35 U.S.C. 154(b) by 962 days.

(21) Appl. No.: 14/773,369

(22) PCT Filed: Mar. 15, 2014

(86) PCT No.: PCT/US2014/029985
§ 371 (c)(1),
(2) Date: Sep. 7, 2015

(87) PCT Pub. No.: WO2014/145253
PCT Pub. Date: Sep. 18, 2014

(65) Prior Publication Data
US 2016/0015586 A1    Jan. 21, 2016

Related U.S. Application Data

(60) Provisional application No. 61/788,592, filed on Mar. 15, 2013.

(51) Int. Cl.
| | | |
|---|---|---|
| *A61G 11/00* | (2006.01) | |
| *A61M 16/20* | (2006.01) | |
| *A61F 7/08* | (2006.01) | |
| *A61M 16/10* | (2006.01) | |
| *A61M 16/16* | (2006.01) | |

(52) U.S. Cl.
CPC ............. *A61G 11/00* (2013.01); *A61F 7/08* (2013.01); *A61M 16/1005* (2014.02); *A61M 16/161* (2014.02); *A61M 16/201* (2014.02)

(58) Field of Classification Search
CPC .............. A61G 1/00; A61G 1/001–009; A61G 2203/723; A61G 1/042; A61G 1/06; A61G 3/006; F16F 15/021; F16F 15/022; F16F 15/1218; F16F 15/1219; F16F 15/126
See application file for complete search history.

(56) References Cited

U.S. PATENT DOCUMENTS

| | | | |
|---|---|---|---|
| 4,934,997 A | 6/1990 | Skakas | |
| 5,534,669 A * | 7/1996 | Schroeder | A61G 11/00 181/198 |
| 6,673,007 B2 * | 1/2004 | Salmon | A61G 11/00 600/22 |

(Continued)

FOREIGN PATENT DOCUMENTS

| | | |
|---|---|---|
| WO | 1999012512 | 3/1999 |
| WO | 2005023164 | 3/2005 |

OTHER PUBLICATIONS

International Search Report PCT/US2014/029985, dated Jul. 7, 2014.

*Primary Examiner* — Carrie R Dorna
(74) *Attorney, Agent, or Firm* — Barnes & Thornburg LLP

(57) ABSTRACT

A shock and vibration system for an infant care transport system with an enclosed infant care device. The shock and vibration system utilizes multiple damping systems that create a floating patient support system that allows the infant care device to move in the various axes of motion instead of being rigidly mounted to the frame or sub-frame, or any substructure.

25 Claims, 8 Drawing Sheets

(56) References Cited

U.S. PATENT DOCUMENTS

2007/0089236 A1* 4/2007 Bailey-Vankuren ..... A61G 1/02
                                                    5/1
2011/0125010 A1   5/2011 Vaquero Lopez et al.
2014/0051910 A1   2/2014 Arnold et al.
2014/0051913 A1*  2/2014 Arnold .................. A61G 11/00
                                                   600/22

* cited by examiner

INFANT CARE TRANSPORT DEVICE WITH SHOCK AND VIBRATION SYSTEM

CROSS-REFERENCE TO RELATED APPLICATIONS

This application is a national stage entry of PCT International Patent Application No. PCT/US2014/029985, filed Mar. 15, 2014, which claims the benefit of U.S. Provisional Patent Application No. 61/788,592, filed Mar. 15, 2013.

BACKGROUND

This disclosure relates to various infant warming and transport devices that are used to protect newborns immediately after birth, and particularly those that are used for transport of the infants either within hospital environments or between hospitals via ground or air transport. In the treatment of infants, and particularly those born prematurely, it is necessary to provide heat to the infant during the care and treatment of the infant and to minimize heat loss from the infant's body. This disclosure will refer to these devices generically as infant care transport devices. They can be called neonatal incubators, infant warmers, neonatal transporters, etc. This disclosure anticipates any of those names.

Such an infant care device is often a rigid box-like enclosure in which an infant can be kept in a controlled environment for observation and care. The infant care device may include a temperature control system, an air circulation system, including a fan, a humidity control system, a control valve through which oxygen may be added, and access ports for nursing care. To facilitate transport this structure is often mounted on a support system that may include wheels.

Infant care transport devices are exposed to shock and vibration effects during movement that transmit those shocks to the patient. In transport systems like neonatal incubators, shock and vibration occurs during loading and unloading of the infant care transport device into the transport vehicle, from rough roads, impacts from take-off and landings in planes and helicopters, movements of the aircraft in-flight, and just movement of the infant care transport device over rough surfaces as well as shock and vibration that occurs inside of the hospital due to thresholds, elevators, and accidental impact of the infant care transport device into walls, etc. These effects can result in serious life threatening injuries to comprised patients, especially premature infants where shock and vibration can cause brain hemorrhages and injury.

There is a need then to provide damping systems to these infant care transport devices that can dampen these shocks and vibrations and to take all axes (x, y, and z) into account.

BRIEF SUMMARY

This need can be met by incorporating multiple shock and vibration damping systems to minimize those conditions being transmitted to the patient. Embodiments that may be included in this approach include a set of z axis dampers incorporated into the main structure, a similar set of dampers for x & y axes, and the addition of a floating patient support system that allow the patient system to move in the axis of vibration instead of being rigidly mounted to the frame as in current systems. The system also adds over-travel protection for extreme conditions to ensure that the free movement of these axes will be limited in extreme conditions as a fail-safe mode.

DESCRIPTION OF DRAWINGS

There are disclosed in the drawings and detailed description to follow various embodiments of the solution proposed herein. It should be understood, however, that the specific embodiments given in the drawings and entailed description do not limit the disclosure. On the contrary, they provide the foundation for discerning the alternative forms, equivalents, and modifications that will be encompassed in the scope of the eventual claims.

DETAILED DESCRIPTION

Figure 1:
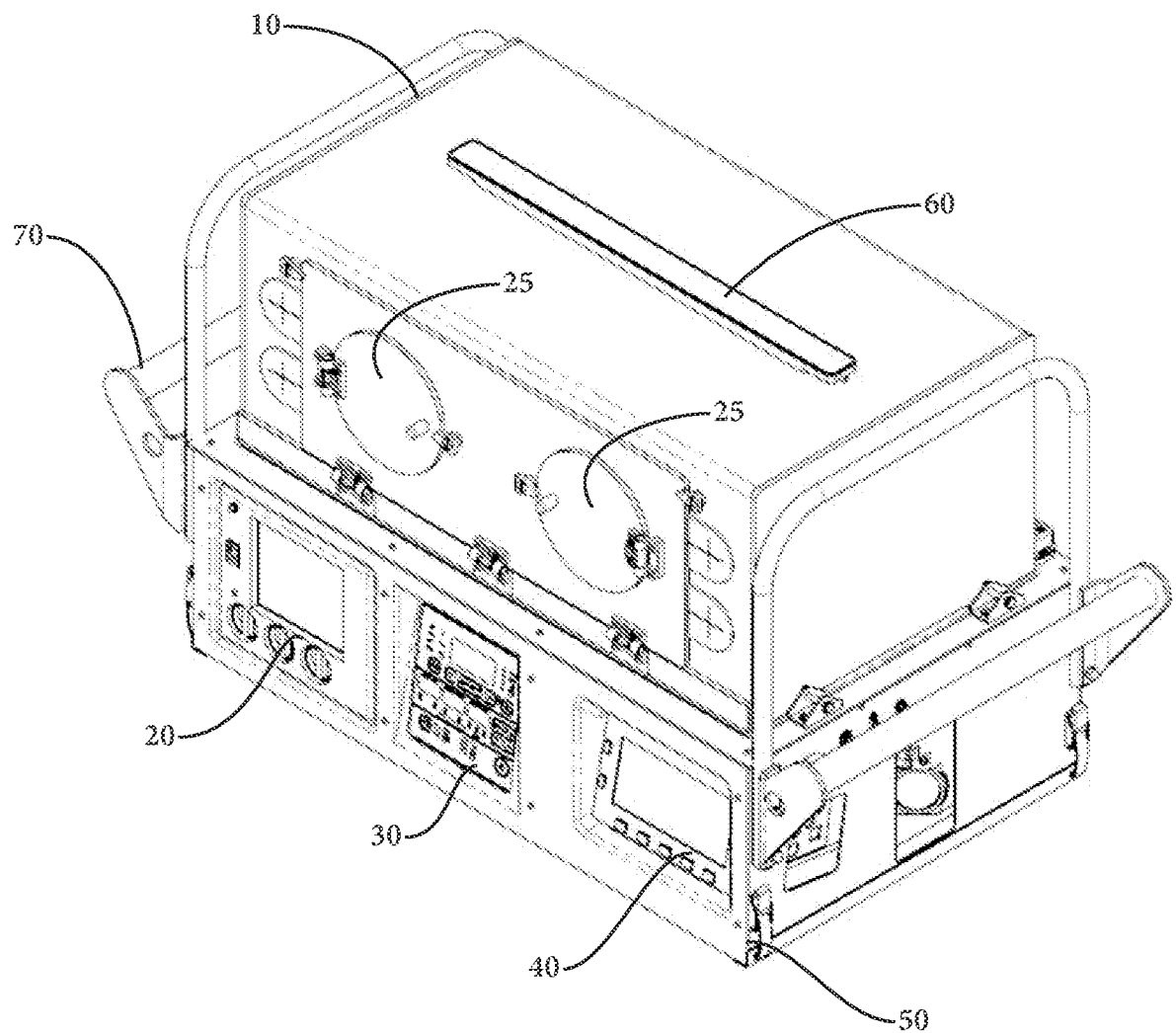
FIG. 1 is a view of an infant care transport device or neonatal incubator that can include the inventive concept to be described in this disclosure.
Figure 2:
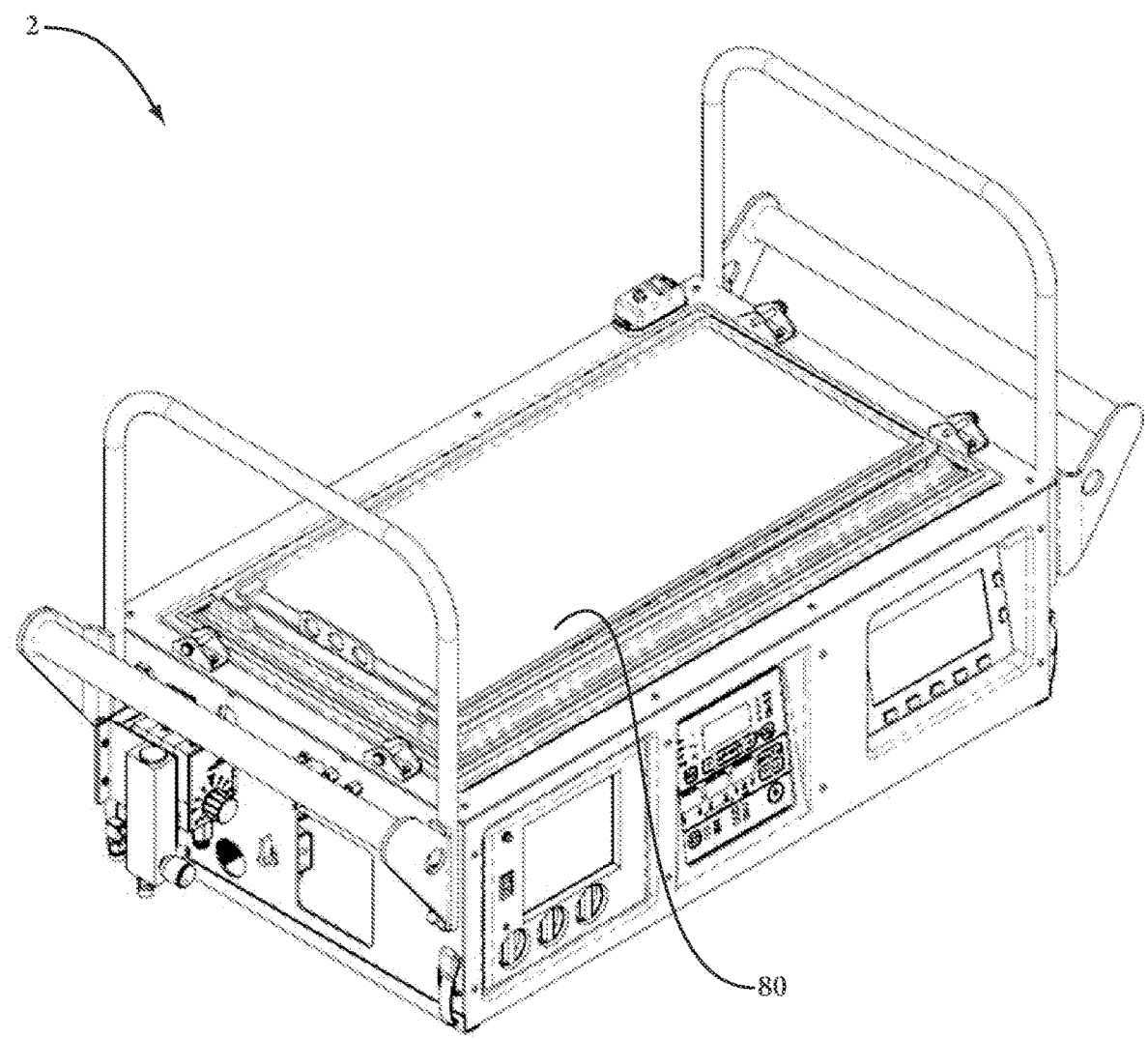
FIG. 2 is an alternate view of an infant care transport device or neonatal incubator that can include the inventive concept to be described in this disclosure.
Figure 3:
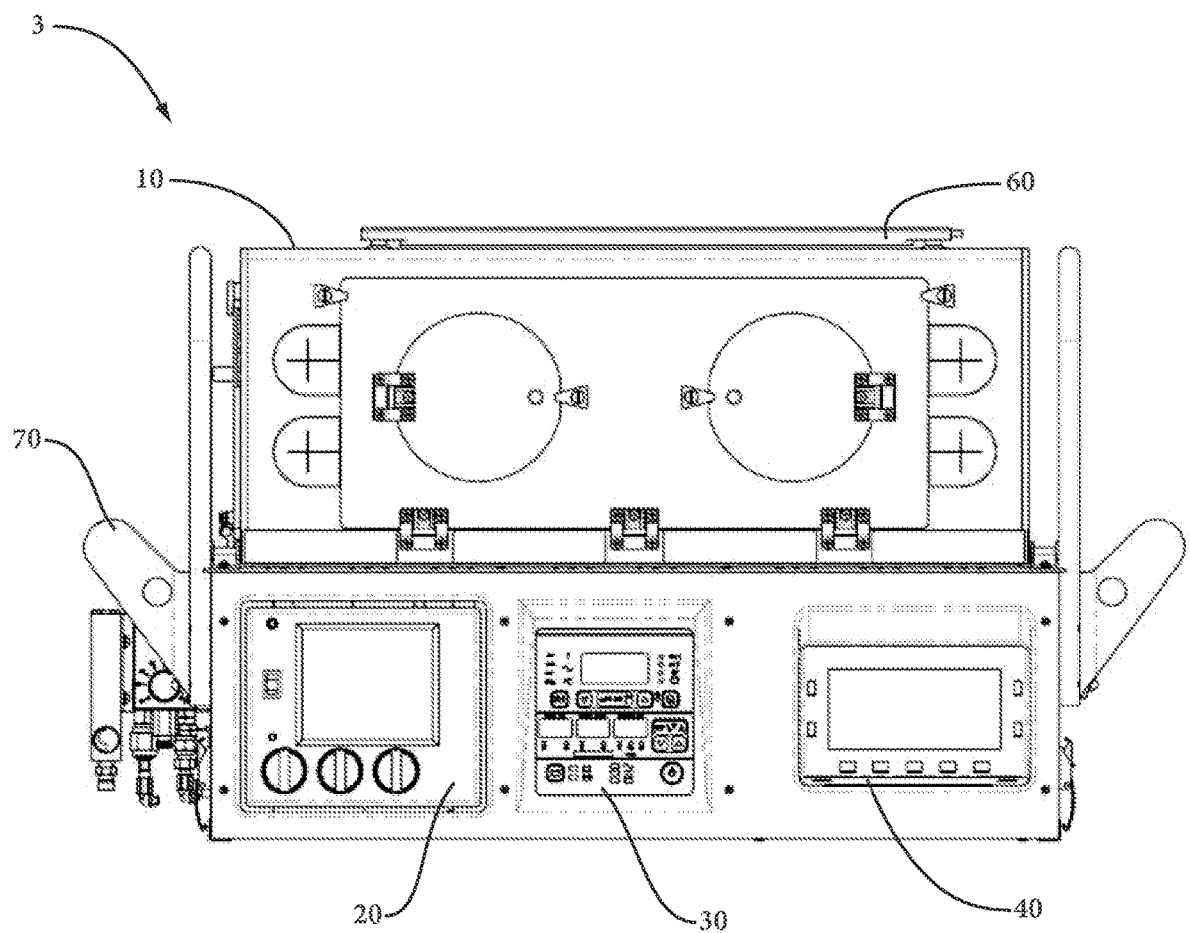
FIG. 3 is an alternate view of an infant care transport device or neonatal incubator that can include the inventive concept to be described in this disclosure.

Referring now to FIGS. 1, 2, and 3, several views of an infant care device or neonatal incubator system that can include the inventive concepts to be described in this disclosure. FIG. 1, shown overall by the numeral 1, is the infant care device. On the side of the infant care device system there is a ventilator system 20, a user interface 30, and a monitor 40. A chamber 10 covering and protecting the patient sits on top, including a light 60 and side ports 25 providing access for care givers.

FIG. 2, represented by the numeral 2, is an alternate view of the same system with the chamber removed, showing the patient support 80 that underlies the infant.

FIG. 3, represented by the numeral 3, is a front view of the same system with the chamber 10 in place, and again showing the ventilator 20, user interface 30, and monitor 40.

Figure 4:
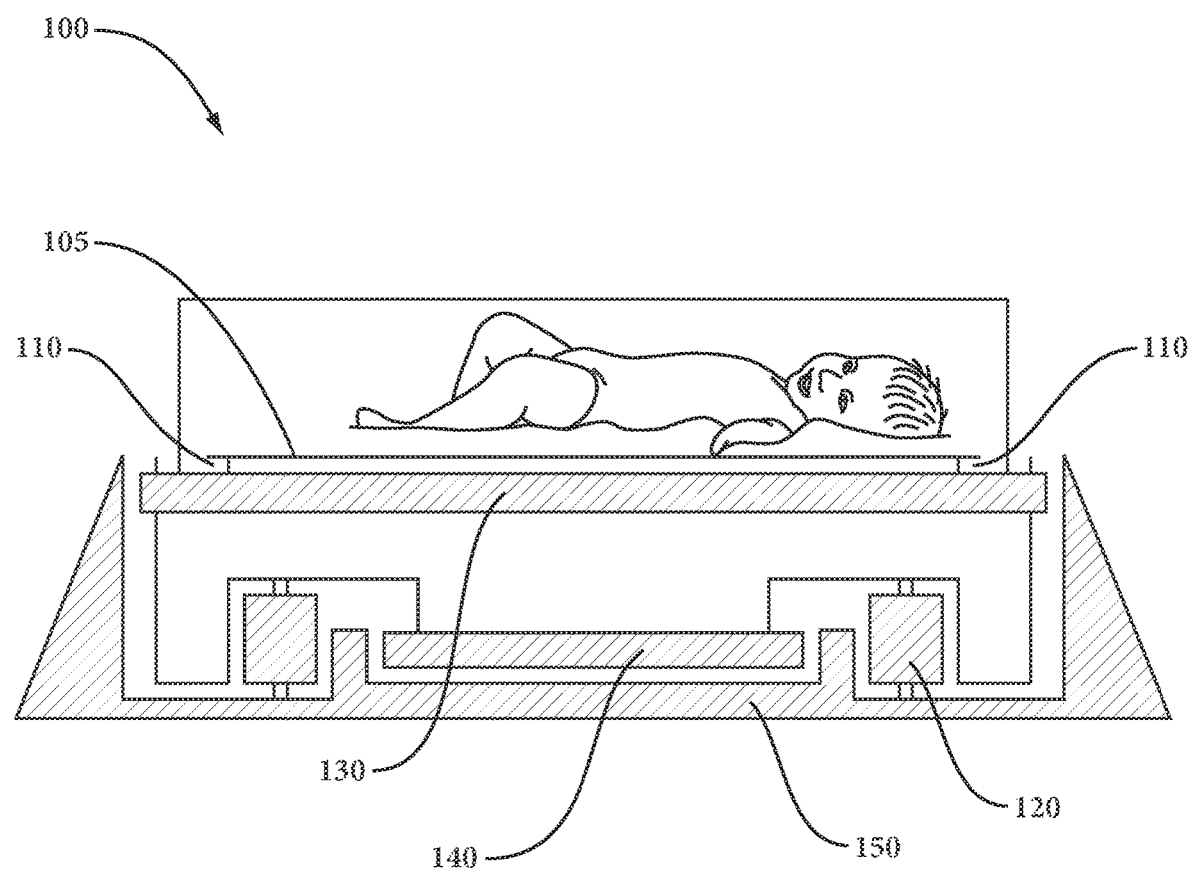
FIG. 4 is a side view illustration of an overall damping system. For an infant care transport device or neonatal incubator.

FIG. 4, represented by numeral 100, illustrates an embodiment of the overall shock and vibration system for an infant care transport device. The system consists of multiple damping systems including one or more z-axis dampers 110 attached to and under a patient support 105 and further attached to the infant care device main frame 130. Z-axis bed dampers 110 dampen z-axis shock and vibration movement between the patient support 105 and the infant care device main frame 130. One or more vertical isolators 120 (z axis) are mounted to a lower sub-frame 150 or directly to a stretcher, cart or other device (not shown) to limit the initial shock transmitted to the system caused by the mounting of the infant care device to another system, and a radial x-y axis damper 140 to limit the lateral (x & y axes) shock and vibration movements to the system.

The radial x-y axis damper 140 can absorb shocks in any direction in the x-y plane. More details of an embodiment of a radial x-y axis damper is shown and discussed in later drawings. The z-axis bed dampers 110 and vertical z-axis isolators 120 can use a variety of damping technologies such as springs, air bladders, bellows, elastomeric materials, magneto-rheological, piezoelectric, or other electronically controlled variable damper system as well as viscous or fluidic type dampers or other art known techniques to absorb these shocks and any of these possibilities are anticipated herein. It most likely will be a combination of materials tuned for the infant care transport device weight and the vibration environment the infant care transport device is subject to.

Each of these separate damping systems can act independently of each other so as not to interfere with the damping of each axis when there is a complex multi-axis shock or vibration that occurs.

It is possible and envisioned that these multiple damping systems could be combined into a single isolator system that multiple independent damping axes contained within it for ease of assembly and manufacturability.

The shock and vibration system also has an over-ride system that acts as a limit stop in cases of extreme situations that might over-drive the system. The combination of these systems creates a floating patient support that is isolated from the infant care device main frame, allowing it to move relative to the direction of shock or vibration.

In another embodiment the shock and vibration system contains a method of locking the damping system so that the axes are no longer free floating.

Figure 5:
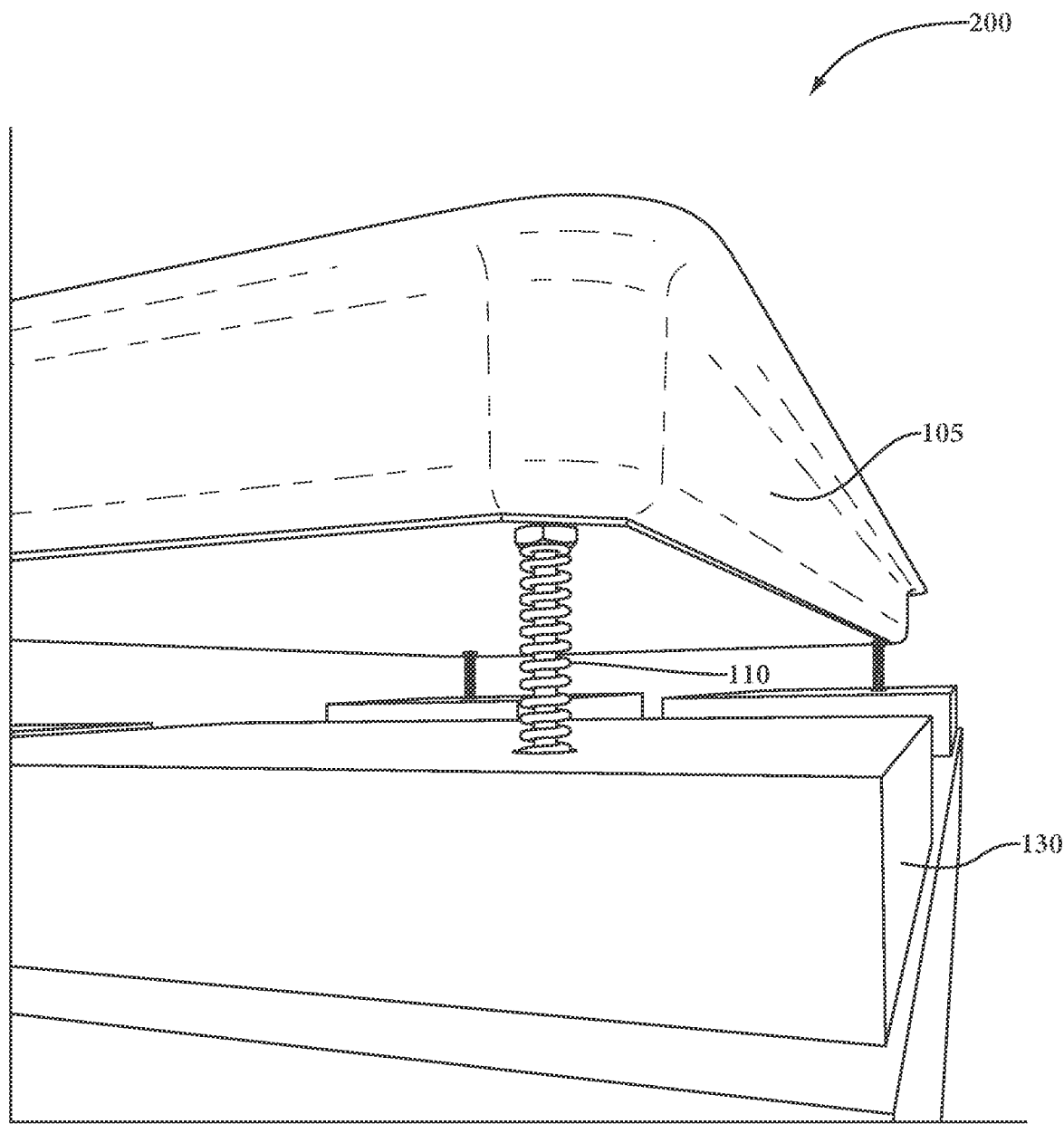
FIG. 5 is a more detailed illustration of a possible patient support z-axis bed damper.

FIG. 5 (numeral 200) illustrates a more detailed example of z-axis bed dampers 110 under a patient support 105. These z-axis dampers are mounted to the infant care transport device main frame 130 in order to create free a floating patient support. For illustrative purposes the z axis bed damper 110 is shown as a spring. However, as mentioned previously this could be a implemented with a variety of damping technologies such as springs, air bladders, bellows, elastomeric materials, magneto-rheological, piezoelectric, or other electronically controlled variable damper systems as well as viscous or fluidic type dampers or other art known techniques to absorb these shocks and any of these possibilities are anticipated in this disclosure.

Figure 6:
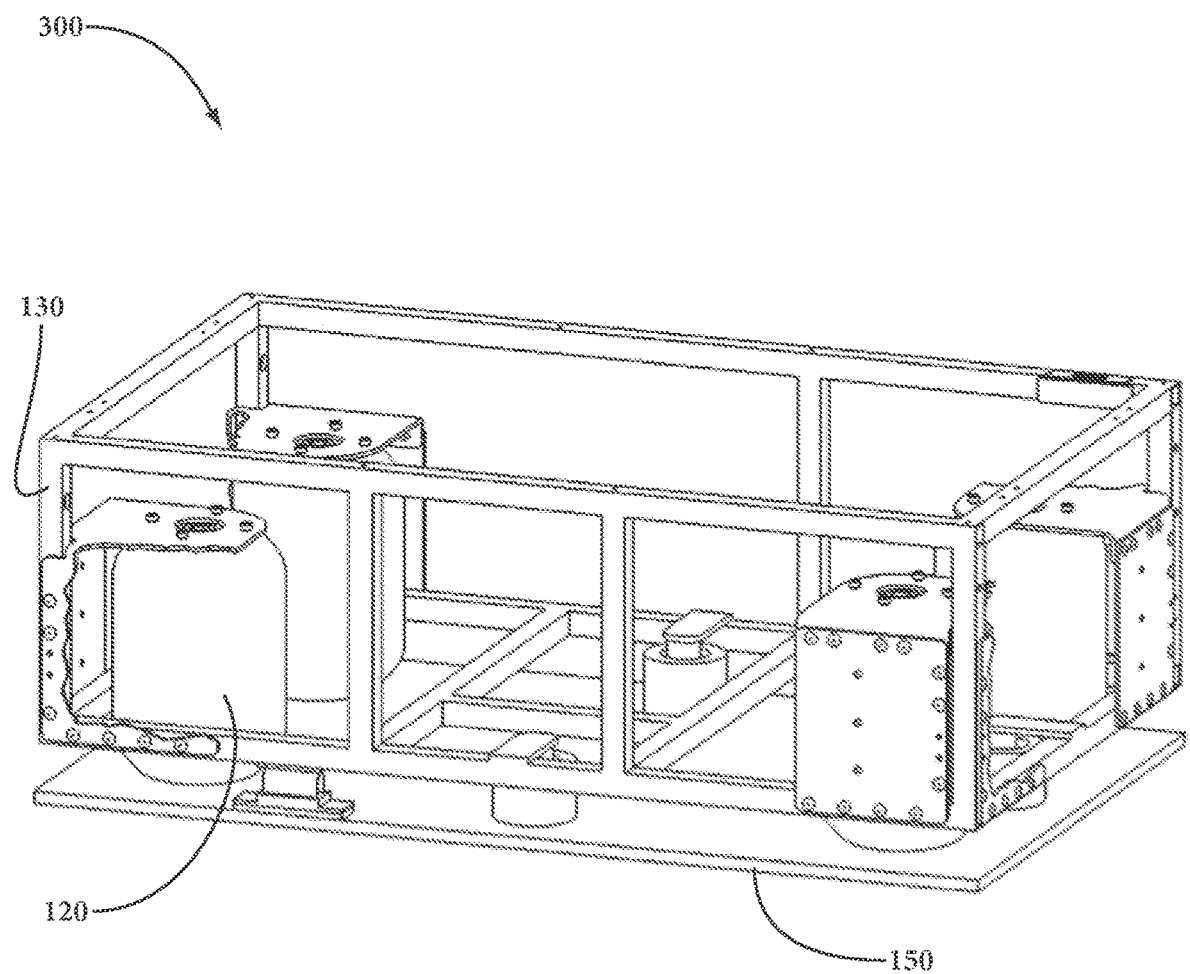
FIG. 6 is a more detailed illustration of z-axis vertical isolators.

FIG. 6 (numeral 300) illustrates an example of vertical z-axis isolators 120 (equivalent to isolators 120 in FIG. 4) that are deployed between the infant care transport device main frame 130 and the lower sub-frame 150. The z-axis isolators reduce the shock and vibration being transmitted from the device the infant care transport device is mounted to, and the infant care transport device main frame. As mentioned previously the vertical z-axis isolators 120 can be any design of damper such as springs, air bladders, bellows, elastomeric materials, magneto-rheological, piezoelectric, or other electronically controlled variable damper systems.

Figure 7:
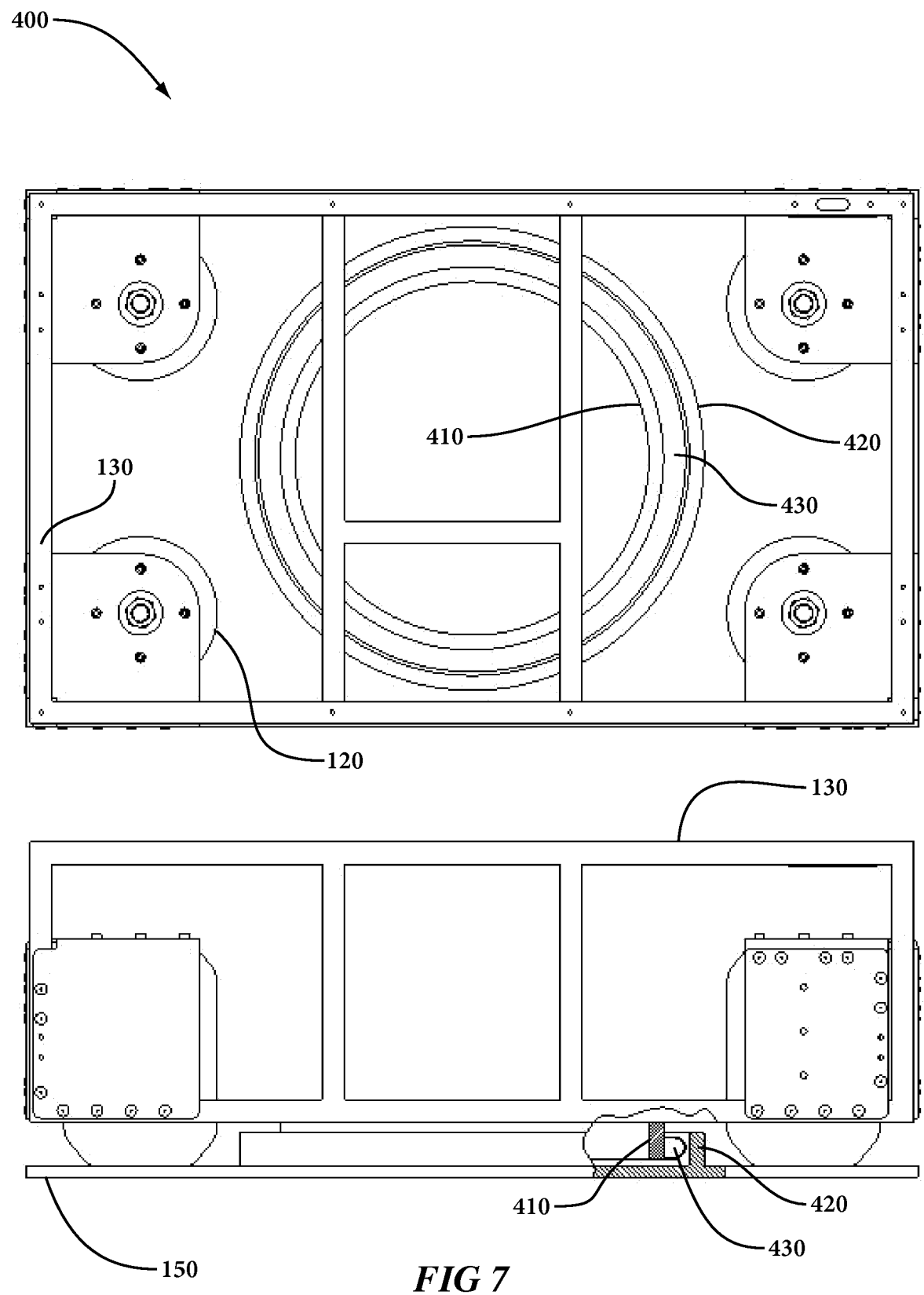
FIG. 7 is a more detailed illustration of a radial damping system to reduce shock and vibration in the x and y axis.

FIG. 7 (numeral 400) illustrates one embodiment of a example of a radial (x-y) axis damper (equivalent to the damper 140 in FIG. 4) that can be deployed between the infant care transport device main frame and lower sub-frame to limit any lateral shock and vibration that occurs in any direction in the x-y plane. Illustrated is a top and side view. A radial damper housing 410 is attached to the infant care transport device main frame 130. This radial damper housing is shown in both the top view and it is shown in the side view in a cut-away. Within this housing 410 is a lateral radial x-y axis damper 430. Surrounding the radial damper housing 410 and attached to the infant care transport device sub-frame 150 is a stop 420. In the drawing illustration the radial damper housing 410, the radial x-y axis damper 430 and the stop 420 that surrounds the housing and damper are shown as completely circular for illustrative purposes, but other shapes, such as elliptical or others could be envisioned. This disclosure anticipates any shape that would surround the radial x-y axis damper with a stop.

In this embodiment the infant care transport device floats radially (in the x-y plane) and does not contact the sub-frame stop 420 until the radial x-y axis damper responds to a possible shock or vibration. The radial damper stop 420 surrounds the radial damper in order to take the forces in any x-y axis direction. The damper could use a variety of damping technologies such as springs, air bladders, bellows, elastomeric materials, magneto-rheological, piezoelectric, or other electronically controlled variable damper system as well as viscous or fluidic type dampers or other art known techniques to absorb these shocks and any of these possibilities are anticipated herein.

It should be recognized that the embodiment described herein regarding the radial x-y axis radial damper could be "fipped" in the sense that the radial damper housing and its enclosed x-y axis damper could be attached to the infant care transport device sub-frame while the "stop" is attached to the infant care transport main frame and still encircling the radial damper housing. This embodiment would operate in the same way to dampen shocks and vibrations in any x-y axis direction.

Figure 8:
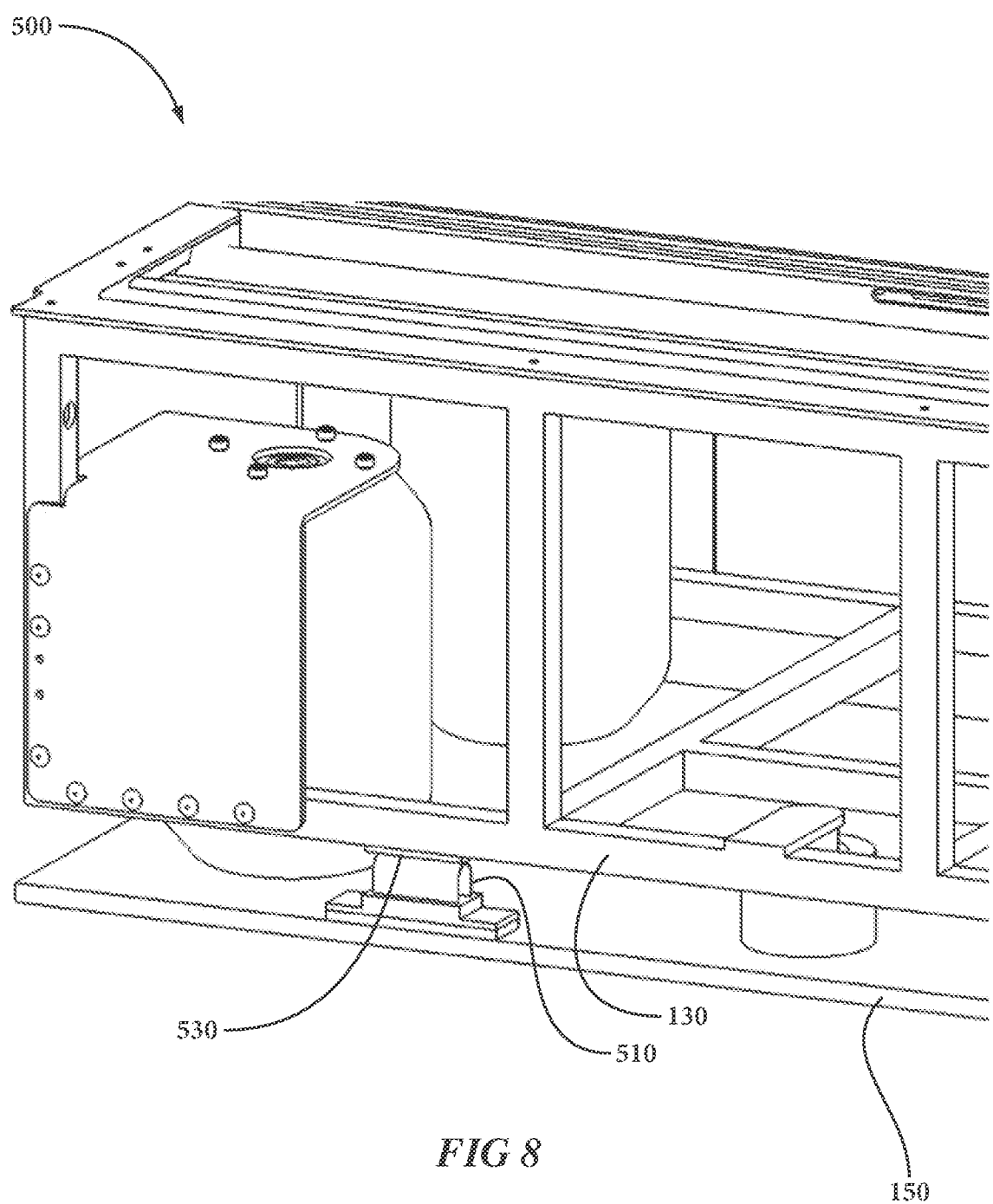
FIG. 8 is an illustration of over-travel protection limits for more extreme shock and vibration conditions.

FIG. 8 (numeral 500) illustrates a more detailed example of the over travel limit springs 510 that are connected to the infant care transport device lower sub-frame 150 that would limit extreme z travel under severe conditions by the spring hitting the hard stop 530 mounted to the infant care transport device main frame 130. The hard stop is a safety measure required to make provisions for an extreme or catastrophic condition that is beyond the capability if the damping systems.

The system described herein reduces the shock and vibration transmitted to the device and patient during transport and movement of the device. Current systems can subject the patient to high levels of shock and vibration under transport conditions that can lead to permanent injury.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

What is claimed is:

1. An infant care transport device with a shock and vibration system, infant care transport device comprising:
    an enclosed infant care device comprising a patient support configured to underlie an infant;
    at least one z-axis bed damper connecting the patient support to an infant care transport device main frame to dampen z-axis vertical movement of the patient support relative to the infant care transport device main frame; and at least one radial x-y axis damper configured to dampen x-y axis movement between the infant care transport device main frame and an infant care transport device sub-frame;

wherein the at least one radial x-y axis damper comprises:
a radial damper housing attached to the infant care transport device main frame but not attached to the infant care transport device sub-frame,
a radial damper positioned within the radial damper housing, and
a stop attached to the infant care transport device-sub-frame and encircling the radial damper housing.

2. The infant care transport device with a shock and vibration system of claim 1, further comprising:
at least one vertical z-axis isolator between the infant care transport device main frame and the infant care transport device sub-frame to dampen z-axis movement.

3. The infant care transport device with a shock and vibration system of claim 2, wherein the at least one z-axis bed damper employs elastomeric materials for damping.

4. The infant care transport device with a shock and vibration system of claim 2, wherein the at least one radial x-y axis damper employs elastomeric materials for damping.

5. The infant care transport device with a shock and vibration system of claim 2, wherein the at least one z-axis isolator employs elastomeric materials for damping.

6. The infant care transport device with a shock and vibration system of claim 2, wherein the at least one z-axis bed damper employs springs for damping.

7. The infant care transport device with a shock and vibration system of claim 2, wherein the at least one radial x-y axis damper employs springs for damping.

8. The infant care transport device with a shock and vibration system of claim 2, wherein the at least one z-axis isolator employs springs for damping.

9. The infant care transport device with a shock and vibration system of claim 2, wherein the at least one z-axis bed damper employs magneto-mechanical, piezoelectric, or other electronically controlled variable damper systems for damping.

10. The infant care transport device with a shock and vibration system of claim 2, wherein the at least one radial x-y axis damper employs magneto-mechanical, piezoelectric, or other electronically controlled variable damper systems for damping.

11. The infant care transport device with a shock and vibration system of claim 2, wherein the at least one z-axis isolator employs magneto-mechanical, piezoelectric, or other electronically controlled variable damper systems for damping.

12. The infant care transport device with a shock and vibration system of claim 2, wherein the at least one z-axis bed damper employs air bladders or bellows for damping.

13. The infant care transport device with a shock and vibration system of claim 2, wherein the at least one radial x-y axis damper employs air bladders or bellows for damping.

14. The infant care transport device with a shock and vibration system of claim 2, wherein the at least one z-axis isolator employs air bladders or bellows for damping.

15. The infant care transport device with a shock and vibration system of claim 2, wherein the at least one z-axis damper and the at least one radial x-y damper are configured to be locked.

16. The infant care transport device with a shock and vibration system of claim 1, wherein the radial damper housing, the radial damper, and the stop of the at least one radial x-y axis damper are circular in shape.

17. The infant care transport device with a shock and vibration system of claim 1, wherein the radial damper housing, the radial damper, and the stop of the at least one radial x-y axis damper are elliptical in shape.

18. The infant care transport device with a shock and vibration system of claim 1, wherein the enclosed infant care device is enclosed with a chamber configured to cover and protect the infant.

19. The infant care transport device with a shock and vibration system of claim 18, wherein the chamber configured to cover and protect the infant comprises side ports providing access to the infant for caregivers.

20. The infant care transport device with a shock and vibration system of claim 1, wherein the enclosed infant care device further comprises a ventilator for maintaining ventilation within the device.

21. The infant care transport device with a shock and vibration system of claim 1, further comprising a heated mattress.

22. The infant care transport device with a shock and vibration system of claim 1, wherein the enclosed infant care device further comprises a control valve through which oxygen can be added.

23. An infant care transport device with a shock and vibration system, infant care transport device comprising:
an enclosed infant care device comprising a patient support configured to underlie an infant;
at least one z-axis bed damper connecting the patient support to an infant care transport device main frame to dampen z-axis vertical movement of the patient support relative to the infant care transport device main frame; and
at least one radial x-y axis damper configured to dampen x-y axis movement between the infant care transport device main frame and an infant care transport device sub-frame;
wherein the at least one radial x-y axis damper comprises:
a radial damper housing attached to the infant care transport device sub-frame but not attached to the infant care transport device main frame;
a radial damper; and
a stop attached to the infant care transport device main frame and encircling the radial damper housing.

24. The infant care transport device with a shock and vibration system of claim 23, wherein the radial damper housing, the radial damper, and the stop of the at least one radial x-y axis damper are circular in shape.

25. The infant care transport device with a shock and vibration system of claim 23, wherein the radial damper housing, the radial damper, and the stop of the at least one radial x-y axis damper are elliptical in shape.

* * * * *